United States Patent
Breziat et al.

(10) Patent No.: US 10,309,168 B2
(45) Date of Patent: Jun. 4, 2019

(54) METHOD FOR CHECKING A SCREWING STATE OF A TUBULAR THREADED SEAL

(71) Applicant: VALLOUREC OIL AND GAS FRANCE, Aulnoye-Aymeries (FR)

(72) Inventors: Nicolas Breziat, Valenciennes (FR); Sebastien Colin, Bantouzelle (FR); Alastair Brodie, Aberdeenshire (GB); Sébastien Petit, Thumeries (FR); Hanae Qozam, Douai (FR)

(73) Assignee: VALLOUREC OIL AND GAS FRANCE, Aulnoye-Aymeries (FR)

( * ) Notice: Subject to any disclaimer, the term of this patent is extended or adjusted under 35 U.S.C. 154(b) by 275 days.

(21) Appl. No.: 14/649,028

(22) PCT Filed: Dec. 16, 2013

(86) PCT No.: PCT/FR2013/053103
§ 371 (c)(1),
(2) Date: Jun. 2, 2015

(87) PCT Pub. No.: WO2014/096663
PCT Pub. Date: Jun. 26, 2014

(65) Prior Publication Data
US 2015/0308201 A1     Oct. 29, 2015

(30) Foreign Application Priority Data
Dec. 18, 2012  (FR) .................................. 12 62191

(51) Int. Cl.
*F16L 15/00*    (2006.01)
*G01N 29/07*    (2006.01)
*E21B 19/16*    (2006.01)

(52) U.S. Cl.
CPC ........... *E21B 19/165* (2013.01); *G01N 29/07* (2013.01); *F16L 15/00* (2013.01); *F16L 15/001* (2013.01); *G01N 2291/011* (2013.01)

(58) Field of Classification Search
CPC ........ E21B 19/165; F16L 15/00; F16L 15/001
See application file for complete search history.

(56) References Cited

U.S. PATENT DOCUMENTS

| 4,080,836 A * | 3/1978 | Thompson | G01N 29/07 73/597 |
| 4,398,421 A * | 8/1983 | White | G01B 17/02 73/597 |

(Continued)

FOREIGN PATENT DOCUMENTS

| AU | 621147 | 3/1990 |
| CN | 201041008 Y | 3/2008 |

(Continued)

OTHER PUBLICATIONS

International Search Report dated Mar. 31, 2014 in PCT/FR2013/053103 filed Dec. 16, 2013.

*Primary Examiner* — Jacob J Cigna
(74) *Attorney, Agent, or Firm* — Oblon, McClelland, Maier & Neustadt, L.L.P.

(57) ABSTRACT

A method for monitoring a makeup state of a threaded connection including a male threaded tubular element and a female threaded tubular element. In the method, during makeup of the male threaded element into the female threaded element, a variation with time of a dimensional characteristic of at least one of the elements is measured in a pre-defined direction. Next, the variation with time of the characteristic is analyzed to determine a makeup state for the threaded connection.

13 Claims, 4 Drawing Sheets

(56) References Cited

U.S. PATENT DOCUMENTS

| | | | | |
|---|---|---|---|---|
| 4,484,475 A | * | 11/1984 | Ogura | G01L 1/255 73/579 |
| 4,569,229 A | * | 2/1986 | de Halleux | G01L 5/246 411/14 |
| 4,601,207 A | * | 7/1986 | Steblay | G01N 29/07 405/259.1 |
| 4,700,576 A | * | 10/1987 | Grare | F16L 15/001 285/93 |
| 4,785,668 A | * | 11/1988 | Pagano | G01N 29/265 73/622 |
| 4,870,866 A | | 10/1989 | Slack | |
| 4,914,952 A | * | 4/1990 | Miyajima | G01N 29/0645 73/598 |
| 4,957,002 A | * | 9/1990 | Coyle, Jr. | B23P 19/066 73/761 |
| 5,170,366 A | * | 12/1992 | Passarelli | G01G 9/00 702/41 |
| 5,233,742 A | * | 8/1993 | Gray | B23P 19/066 29/237 |
| 5,461,905 A | * | 10/1995 | Penisson | G01M 3/36 73/46 |
| 6,070,466 A | * | 6/2000 | Taran | G01B 17/02 73/620 |
| 8,438,926 B2 | * | 5/2013 | Hoshino | G01N 29/11 73/598 |
| 2005/0256676 A1 | | 11/2005 | Ales et al. | |
| 2008/0022772 A1 | | 1/2008 | Ales et al. | |
| 2008/0087088 A1 | | 4/2008 | Ales et al. | |
| 2009/0282921 A1 | | 11/2009 | Hoshino et al. | |
| 2009/0314087 A1 | | 12/2009 | Ales et al. | |
| 2012/0067127 A1 | * | 3/2012 | Hoshino | G01N 29/11 73/600 |
| 2014/0116687 A1 | | 5/2014 | Ruehmann | |

FOREIGN PATENT DOCUMENTS

| | | |
|---|---|---|
| JP | 63298054 A | 12/1988 |
| JP | 06-221475 A | 8/1994 |
| JP | 2010-197273 A | 9/2010 |
| SU | 905778 A1 | 2/1982 |
| SU | 1420520 A * | 8/1988 |
| WO | 2008/029957 A1 | 3/2008 |

* cited by examiner

METHOD FOR CHECKING A SCREWING STATE OF A TUBULAR THREADED SEAL

The present invention relates to a method for monitoring makeup of a threaded tubular connection, in particular for oil or gas working. More particularly but not exclusively, it applies to connecting threaded tubular connections known as "premium" connections.

Threaded tubular connections of this type generally comprise a male threaded element at the end of a first great length tube and a female threaded element at the end of a second tube that may be a great length tube or a coupling. When connecting two great length tubes, this is known as an integral connection and as a threaded and coupled connection in the case of connecting two tubes by a coupling.

In the particular case of "premium" threaded connections, the male and female threaded elements each have respectively male and female sealing surfaces and shoulder abutments intended to cooperate when the connection is being made up.

Such threaded connections are in particular used to constitute casing strings or tubing strings or drill pipe strings for hydrocarbon wells or similar wells such as geothermal wells, for example.

Tubes of this type are generally connected vertically, the free end of the string at the surface comprising a female threaded element having an internal female threading.

In order to drop the string into the well, a new tube is positioned above the string provided with a male threaded element comprising an external male thread corresponding to the female threading at the free end of the string, the male threading of the new tube is engaged in the corresponding female thread of the string and the new tube is made up until a pre-defined makeup torque is reached.

The pre-defined makeup torque has to allow the connection to satisfy certain criteria which also depend on the characteristics of the connection itself. In particular, it is important, in the case of "premium" connections, and thus including sealing surfaces, to ensure that the amount of makeup torque applied is defined in order to obtain a contact pressure for the sealing portions which ensures a sufficient seal of the connection while avoiding plastification of those portions.

As a consequence, it is necessary to monitor the amount of this makeup torque with precision.

In the prior art, in particular in document JP 6-221475, a method for monitoring the makeup state of a threaded tubular connection is already known in which during the makeup operation, the amplitude of the torque is analysed as a function of the number of makeup turns made. As illustrated in the figure in that document, the curve exhibits three characteristic portions, corresponding to three makeup states for the connection: the first portion corresponds to a first makeup state during which interference between the threadings occurs, the second portion corresponds to a second makeup state during which interference between the sealing surfaces occurs, and finally, the third portion corresponds to a third makeup state during which the abutments of the two threaded tubes are in contact and under compression. Clearly, other profiles exist in the prior art; in particular, it is possible for a curve to represent the variation in amplitude as a function of the number of makeup turns exhibiting only two distinct slopes rather than three.

However, certain defects present on the threaded elements may cause a sudden rise in the makeup torque during makeup of the elements. The prior art method suffers from the disadvantage that such a rise in the torque could be erroneously interpreted as corresponding to the makeup state for compression of the abutments, whereas in reality, the connection is still in its first makeup state and is not sealed. In the same manner, in contrast, some defects may also cause a variation in the profile of the torque which cannot be interpreted or is difficult to interpret and the connection, albeit made up properly, might be rejected. As a consequence, this presents problems as regards safety and productivity on oil platforms.

Thus, there is a need for a method for monitoring the makeup of two threaded tubular elements which can be used to provide a highly reliable, sealed threaded connection.

To this end, the invention provides a method for monitoring a makeup state of a threaded tubular connection, the threaded connection comprising a male threaded tubular element and a female threaded tubular element, characterized in that during makeup of the male threaded element into the female threaded element, a variation with time of a dimensional characteristic of at least one of the elements is measured in a pre-defined direction and the variation with time of the characteristic is analysed in order to determine a makeup state for the threaded connection.

The invention draws upon the fact that the threaded elements undergo characteristic deformations over the makeup period corresponding to particular makeup states of the connection. Thus, for example, when the male element is made up into the female element, this latter initially undergoes axial compression corresponding to interference of the threadings and the sealing surfaces, then when the abutments come into contact, the female element undergoes an elongation in the axial direction, which increases with compression of the abutments.

A study of these deformations can be used to define a deformation time signature (elongation and/or compression) of the element during makeup in the pre-defined direction. Clearly, several signatures of the same element may be defined in several directions in order to obtain more information regarding the makeup state of the connection.

Thus, an analysis of the variation with time, i.e. during makeup of the connection, of the dimensional characteristic of the element under consideration, i.e. deformation, can be used to determine a makeup state of the connection.

By dimensional characteristic, we mean in the present invention a dimension of a portion of one of the elements depending on a pre-defined direction, for example a length or a width of this portion.

Preferably, this dimensional characteristic is measured using an ultrasound signal. This means of measuring has the advantage of being non-destructive.

Preferably, in order to measure the dimensional characteristic, the ultrasound signal is emitted into the body of the element and the propagation time for the round trip of that signal is analysed in the pre-defined direction. Because of the simple relationship linking the propagation time of a signal with distance, knowing the rate of propagation of the sound wave in the material in question, it is easily possible to determine a dimensional characteristic for the connection.

Preferably, halting makeup of the connection is managed as a function of the measurement of the dimensional characteristic. This means that the instantaneous makeup state of the connection can be taken into account rather than a makeup state based on empirical results.

Preferably, at least one zone with a change of slope is identified in the profile of the variation in the dimensional characteristic and a correspondence is established between this zone and a makeup state of the threaded connection.

As an example, a correspondence may be established between a zone with a change of slope and contact of the two functional portions of the connection, such as shouldering of the abutments or contact of the sealing surfaces.

Furthermore, a method in accordance with the invention may comprise one or more of the following characteristics:

the dimensional characteristic represents a thickness in a substantially radial pre-defined direction or a length in a substantially axial pre-defined direction of the threaded element;

the dimensional characteristic is measured in a portion of the threaded element comprising a sealing surface and/or a shoulder abutment;

the variation in the dimensional characteristic corresponds to elongations and/or contractions of the element in the pre-defined direction;

in order to establish this correspondence, a profile of the variation is modelled using a mathematical method, for example the finite element method, and the measured profile of the variation is compared with the model profile;

the female element belongs to a substantially symmetrical coupling connection of the female/female type and the male element belongs to one end of a great length tube, or the female element and the male element each belong to one end of a great length tube.

The invention also provides a method for connecting a connection, in which a female element and a male element are connected by makeup, characterized in that the monitoring method in accordance with the invention is carried out.

Preferably, stopping makeup of the connection is managed as a function of the measurement of the dimensional characteristic.

The invention also concerns a device for monitoring a makeup state of a threaded tubular connection, the threaded connection comprising a male threaded tubular element and a female threaded tubular element which are capable of cooperating by makeup of the female element into the male element, characterized in that it comprises means for measuring a variation with time of a dimensional characteristic of at least one of the elements in a pre-defined direction and means for analysing the variation with time of the characteristic in order to determine a makeup state of the threaded connection.

Preferably, the monitoring device comprises means for managing stopping of the makeup of the connection as a function of the measurement of the dimensional characteristic.

This feature has the advantage of meaning that managing of the makeup of the connection is very precise, since it is based on actual physical values which are measured instantaneously rather than on control based on empirical values.

A device in accordance with the invention may also include the feature whereby the measuring means comprise at least one ultrasound transducer.

Finally, the invention provides a guidance device for a first threaded tubular element during connection thereof by makeup with a second threaded tubular element, comprising a head for gripping the first tubular element, characterized in that the device comprises a housing for means for measuring a variation with time of a dimensional characteristic of the first tubular element arranged at least partially in the gripping head in order to allow the monitoring method in accordance with the invention to be carried out.

A guidance device of this type is frequently known as a stabbing guide. Conventionally, such a device is used to allow tubular elements forming the connection to be guided into the hole of the oil working set-up. The advantage of the device of the invention is that it allows rapid and simple determination of the makeup state of the connection which is very easy to install.

As an example, the measuring means are housed in the gripping head of the stabbing guide, which means that it can be put in position rapidly and the measuring means are efficiently held on the connection. Furthermore, this has the advantage of not requiring any supplemental equipment in order to form a support for the measuring means.

Preferably, the gripping head comprises an internal cylindrical surface which is capable of surrounding the first element during connection thereof with the second element, the housing forming a hole in the gripping head opening onto the internal cylindrical surface.

Further characteristics and advantages of the invention will become apparent from the following description made with reference to the accompanying drawings and in which:

FIG. 1 illustrates a device for monitoring a threaded connection in accordance with the method of the invention;

FIG. 2A diagrammatically illustrates, in a longitudinal sectional view, a portion of a connection of two symmetrically disposed threaded connections;

Figure 1:
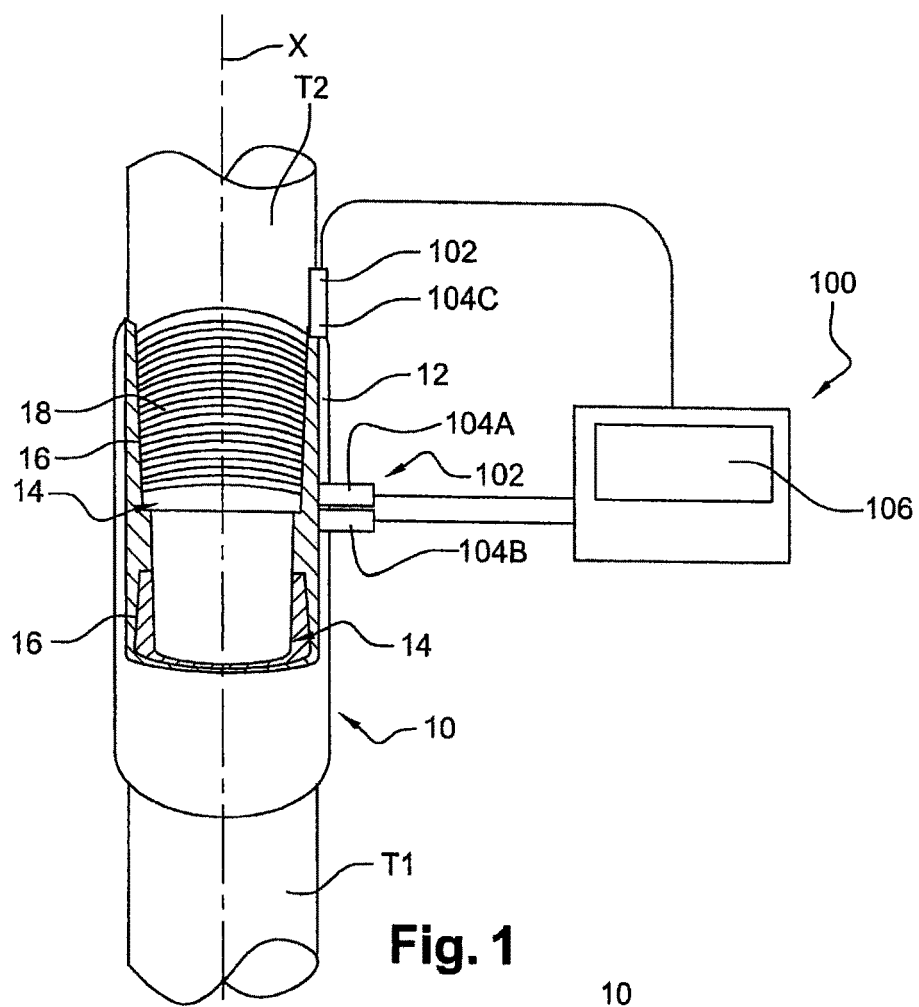

FIG. 1 diagrammatically shows a monitoring device for carrying out a method in accordance with the invention for monitoring a makeup state of a threaded connection of connected tubulars. The device has general reference number 100 and the tubular connection have reference numeral 10.

As illustrated in FIG. 1, the tubular connection 10 is of the coupling type. The connection 10 comprises a coupling connection 12 for two great length tubes T1 and T2 with an axis of revolution X and defines symmetrical first and second threaded connections 14. Only one of the two threaded connections will be described below, for example the threaded connection 14 formed by the coupling 12 and the tube T2.

The term "great length tube" means tubes several meters long, for example approximately ten meters long.

Conventionally, the threaded connection 14 comprises a first tubular threaded element 16 which is female in type and a second tubular threaded element 18 which is male in type. In this example, the first female threaded tubular element 16 belongs to the coupling connection 12 of the female/female type and the male threaded element 18 belongs to one end of the great length tube T2.

In a variation, not shown in the figures, the female element 16 and the male element 18 may also each belong to one end of a "great length tube". In this case, it is known as an "integral connection".

Preferably, the tubes T1 and T2 can be formed from any type of non-alloy, light alloy or high alloy steel, or even from ferrous or non-ferrous alloys, in order to suit different service conditions: the degree of mechanical loading, or the corrosive nature of the fluid inside or outside the tubes.

Figure 2A:
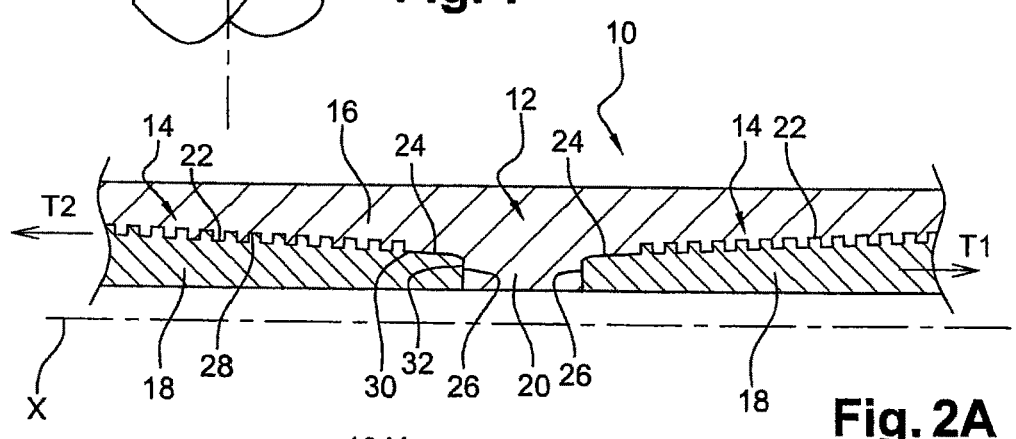
FIG. 2B is a simplified layout of the connection of FIG. 2A, showing a portion of the monitoring device of FIG. 1.

FIG. 2A shows a section through the tubular elements of FIG. 1. As can be seen in this figure, the male threaded elements 18 are respectively connected by makeup into the female threaded elements 16 of the coupling connection 12 to constitute two symmetrical threaded connections 14 connected by a lug 20. This lug 20 is generally a few centimeters long. Preferably, the lug 20 of the coupling 12 has an internal diameter which is substantially identical to that of tubes T1 and T2 such that the flow of the fluid moving inside it is not perturbed.

As illustrated in FIG. 2A, the interior of the female threaded element 16 comprises a female threading 22 and a non-threaded portion extending between the threading 22 and the lug 20. Preferably, the female threaded element 16 also comprises a sealing surface 24 and a shoulder abutment 26. Thus, the non-threaded portion in particular comprises an annular surface with an orientation that is substantially transverse to the abutment forming the shoulder 26 at the end of the lug 20 and a conical bearing surface following the shoulder forming the sealing surface 24.

Similarly, the male threaded element 18 preferably comprises a sealing surface 30 and a shoulder abutment 32. As was the case for the female threaded element, the sealing surface extends, after the male threading 28, into a non-threaded portion of the male element 18. This non-threaded portion comprises an annular surface with a substantially radially orientated abutment forming the male shoulder 32 and a tapered bearing surface following the shoulder forming the sealing surface 30.

After complete makeup of the male threading 28 into the female threading 22, the male 32 and female 26 abutment surfaces bear against each other while the male 30 and female 24 bearing surfaces radially interfere and are thus under metal-to-metal contact pressure. These bearing surfaces thus constitute sealing surfaces that provide the threaded connection with a seal, even at high internal or external fluid pressures and under a variety of loads (axial tension, axial compression, bending, torsion, etc.).

This FIG. 1 also shows a device 100 for monitoring a makeup state of a threaded tubular connection. In accordance with the invention, this device comprises means 102 for measuring a dimensional characteristic of one of the first or second tubular elements. In this example, as illustrated in FIG. 1, the means 102 are arranged in order to measure a dimensional characteristic of the female tubular threaded element 16. Clearly, in a variation which is not shown, the means 102 may also be arranged to measure a dimensional characteristic of the male threaded tubular element.

These measuring means 102 preferably comprise at least one unit for measuring the dimensional characteristic. Preferably and as illustrated, the measuring means 102 comprise three measuring units 104A, 104B and 104C respectively for first, second and third dimensional characteristics. Preferably, each measuring unit comprises an ultrasound transducer. In conventional manner, the ultrasound transducer comprises an ultrasound wave emitter and receiver.

As an example, the emitter and the receiver are located in the same casing. In conventional manner, the emitter emits a train of waves which will be reflected from an object to be detected and then return to the receiver. The time "T" taken to make a round trip can be used to determine the distance "d" of the object with respect to the source (the transducer) using the equation:

$$d = v \times T$$

In this example, the ultrasound signal is emitted inside the body of the threaded tubular element and the propagation time T of this round trip signal is analysed. In this example, v is the speed of sound in the material constituting the tubular elements, and the object to be detected (i.e. the interface reflecting the ultrasound wave) is a tube/air interface.

Further, and preferably, each transducer 104 is arranged against the external tubular surface of the female threaded element 16. As an example, the transducer casing includes a magnetized surface which can be fixed against the tubular surface of the female element.

Figure 2B:
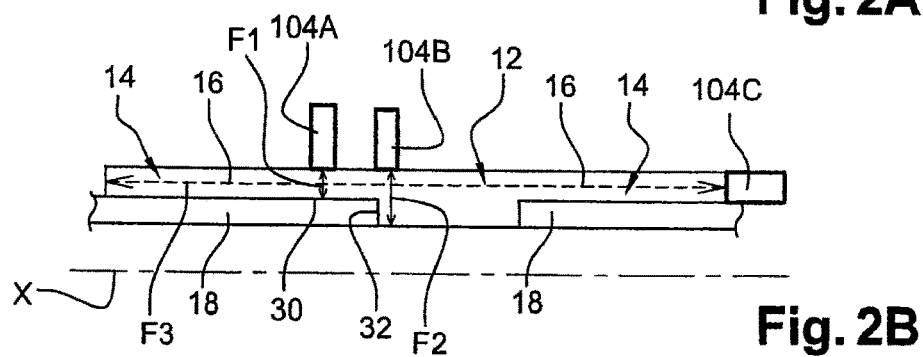

In the example described, the first, second and third dimensional characteristics are each represented diagrammatically by a double-headed arrow (FIG. 2B).

More precisely, in this example, the first characteristic corresponds to a thickness in a substantially radial predefined direction in a portion of the female element 16 comprising the sealing surface 24 (arrow with reference F1) and the second dimensional characteristic corresponds to a thickness in the same radial direction but in a portion of the element 16 comprising the abutment 26 (arrow with reference F2). In fact, the surface 24 and the shoulder abutment 25 are deformed during makeup in a characteristic manner, as has been observed by the inventors. The variation in the dimensional characteristic corresponds to elongations and/or contractions of the female element in the pre-defined direction.

The third dimensional characteristic corresponds to a length in a substantially axial pre-defined direction of the threaded element 16 (arrow with reference F3). In the same manner, the female threaded element 16 is deformed during makeup in the direction of its length in a characteristic manner. Preferably, this third characteristic corresponds to the total length of the coupling comprising the female element in the upper portion of this element, i.e. the longest portion extending axially above the lug of the female element.

Figure 5:
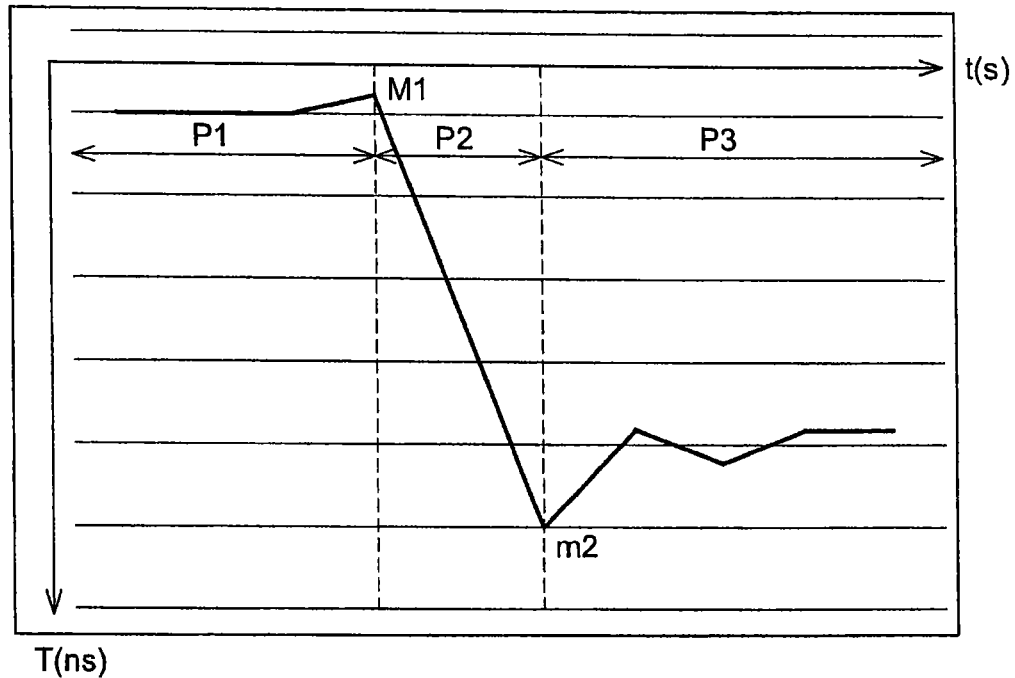
FIGS. 5 to 7 represent curves showing the variation of a dimensional characteristic as a function of time.
Figure 6:
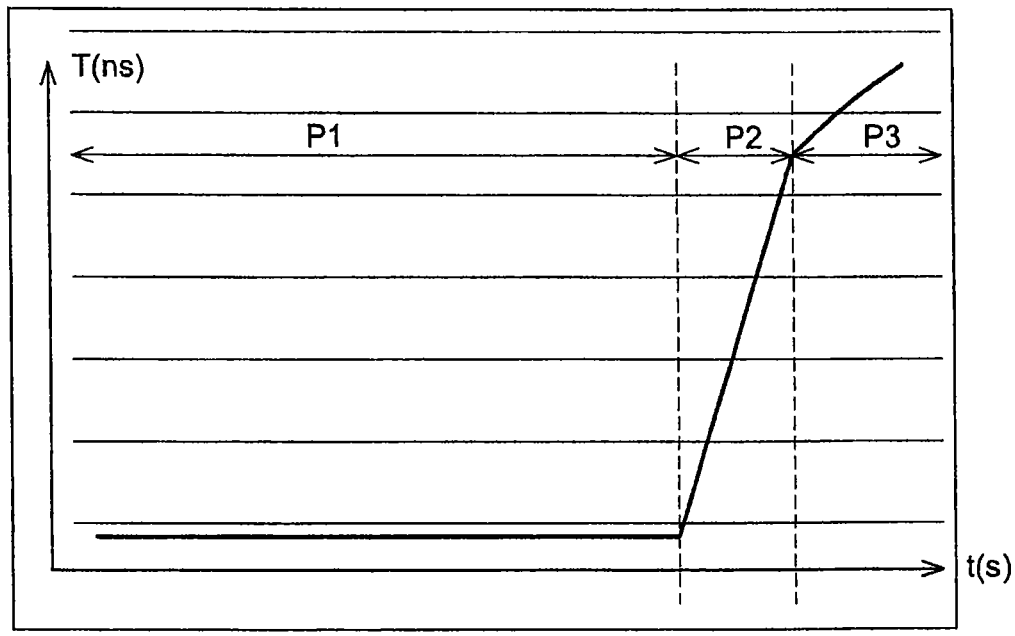
Figure 7:
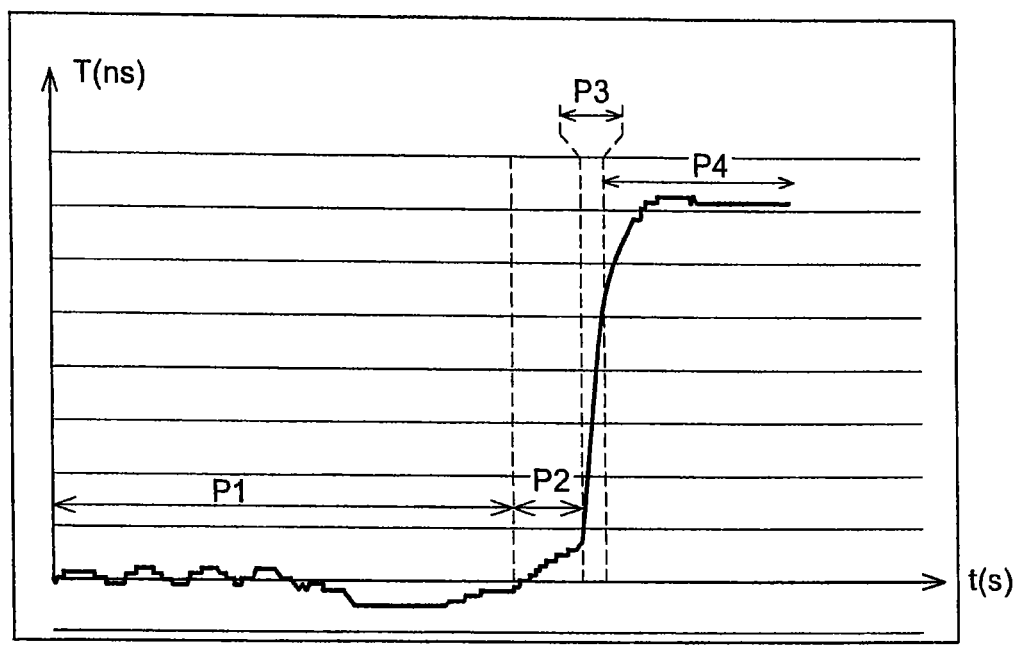

Further, the curves of the variation of the measurement of the three dimensional characteristics of the female threaded element are respectively shown in FIGS. 5, 6 and 7. These curves represent the change in the round trip propagation time T for the ultrasound signal (in nanoseconds (ns)) as a function of the time t (in seconds(s)).

FIG. 5 thus represents the variation with time of the first dimensional characteristic measured by the transducer 104A at the sealing surface. This curve initially has a horizontal portion then the curve varies slowly with a positive slope upwards to a maximum "M1" (period P1). The curve has a sudden change of slope and the curve then varies very rapidly with a negative slope to a minimum "m2" (period P2). The curve then exhibits a third period P3 comprising zigzags.

From a physical viewpoint, the period P1 identified corresponds to radial elongation of the female element 16 at its sealing surface 24 (P1) due to the introduction of the male element 18 into the female element 16, which will cause an axial compression and thus a slight radial expansion of the female element 16. This elongation thus has the result of increasing the time of the round trip for propagation of the signal. The second period P2 is initiated when the sealing surfaces 24 and 30 of the male 18 and female 16 elements come into contact: at this moment, the radial thickness at the sealing surface is reduced rapidly. The third period P3 corresponds to shouldering of the abutments: at this moment, the radial thickness at the sealing surface 24 increases again due to axial compression of the coupling by the male tubular element.

FIG. 6 represents the variation in the second dimensional characteristic as a function of time and thus during makeup measured by the transducer 104B. This curve also has three periods, P1 to P3: the curve thus initially exhibits a zero slope (P1), then the curve varies very rapidly (P2) with a positive slope, then more slowly (P3).

Physically, the first period P1 corresponds to an absence of contact between the two male 32 and female 28 shoulder abutments and no deformation of this portion is apparent; the signal propagation time is constant. The second period P2 corresponds to an elongation of the thickness at the female abutment, linked to compression of the female element 16 by the male element 18, which has a tendency to deform the lug of the female element 16 in the radial direction. Finally, the third period P3 has a lower slope and corresponds to the onset of plastification of the abutments 32 and 26.

FIG. 7 represents the variation with time of the third characteristic measured by the transducer 104C. This curve exhibits four periods, P1 to P4. The first period P1 exhibits a near-zero slope, plus background noise. The second period P2 exhibits a positive slope, then the third period P3 corresponds to a sudden substantially linear variation in the curve to a period P4 corresponding to a non-linear variation.

Physically, the period P1 shows an irregular deformation in the direction of the length of the threaded element. This can be explained by the fact that only the threadings are in contact in this period. The deformation essentially takes place in the radial direction. The changeover from the period P1 to the period P2 corresponds to the sealing surfaces coming into contact. This causes a slight elongation of the female element. During the changeover from the period P2 to the period P3, the abutments come into contact. Compression of the abutments against each other will have the effect of causing a highly characteristic elongation of the female element in the axial direction. This elongation takes place in the elastic domain of the female element, which explains a portion of the curve in the period P3 which is substantially linear. Finally, deformation of the female element 16 reaches the elastic limit of the material constituting it and the behaviour of the curve becomes non-linear in the fourth period P4.

Thus, it is possible to establish a correspondence between a change of slope of the curve of the variation and a makeup state of the threaded connection. The term "makeup state of a threaded connection" principally means a state selected from the following states: engagement of threadings, contact of abutments, contact of sealing surfaces, onset of plastification. However, other makeup states may be identified in these curves of the variations without departing from the scope of the invention.

Preferably, the device 100 also comprises means 106 for analysing the measured curve of the variation. These analysis means 106 are capable of identifying, in the profile of the variation of the dimensional characteristic, at least one slope change zone and of establishing a correspondence between this zone and a makeup state of the threaded connection.

Preferably, in order to establish a correspondence between these various slope change zones and a makeup state of the threaded connection, a model of the profile of the variation is produced using a mathematical method, for example the finite element method, and the analysis means are capable of comparing the measured profile of the variation and the model profile.

Furthermore, for example, the makeup set-up comprises working tongs (not shown). Thus, the threaded connections are generally made up into position with the aid of mechanical or hydraulic machines known as working tongs, which are capable of developing large torques since the threaded connection has to be made up beyond shouldering of the axial abutment surfaces.

In the prior art, the tongs stop when a given makeup torque is reached (nominal torque). However, because of the inertia of the tongs, the actual torque obtained may be shifted with respect to the desired nominal torque. This shift depends on a number of factors and may be reduced by reducing the makeup speed, which has a deleterious effect on makeup productivity.

Preferably, the device 100 comprises means (not shown) for managing halting of the makeup of a connection as a function of the measurement of the dimensional characteristic. Preferably, the means manage the working tongs of the connection as a function of a pre-defined value reached by the dimensional characteristic, for example provided by the analysis means 106 described above. This means that good reliability can be obtained in monitoring makeup, meaning that any excessive tightening of the connection can be avoided, while guaranteeing a sufficient seal. Advantageously, controlling makeup as a function of a measurement of the elongation or contraction of a portion of the connection means that its own characteristics can be taken into consideration. Thus, this means that the empirical criteria conventionally used in the field which do not take into account the particular properties of each connection can be dispensed with.

Figure 3:
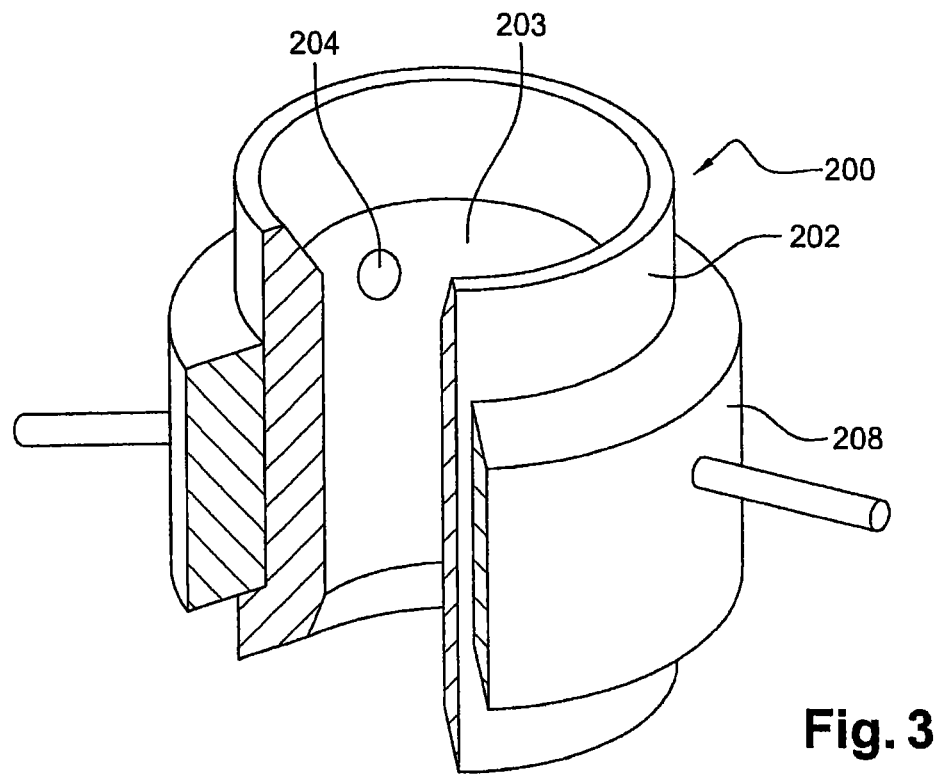
FIG. 3 represents a partially cutaway perspective view of a stabbing guide type guidance device for carrying out the method of the invention.
Figure 4:
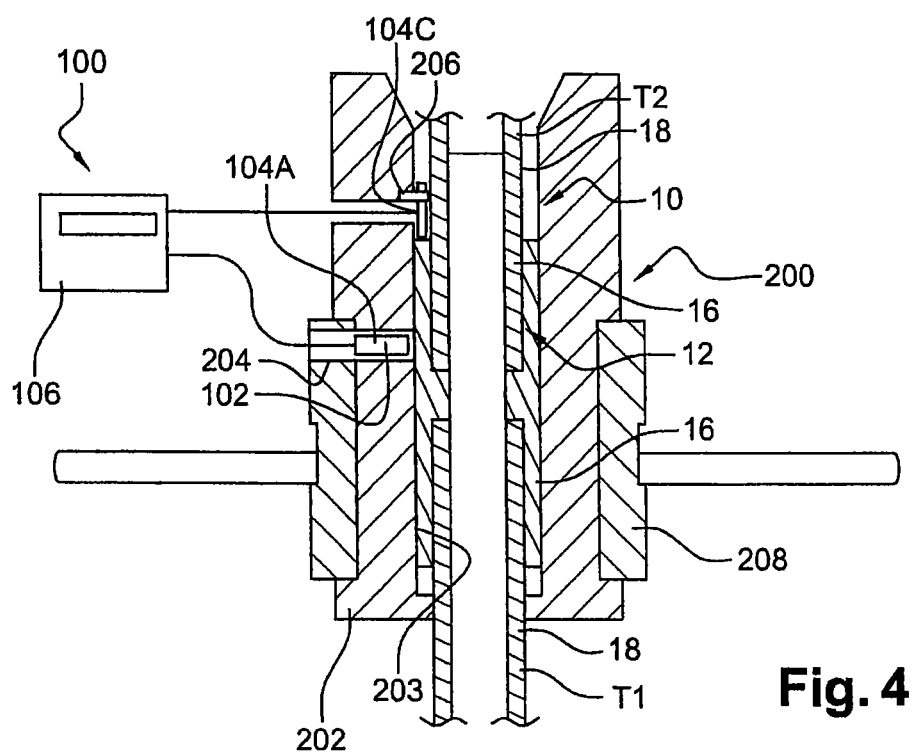
FIG. 4 represents a sectional view of the device of FIG. 3.

FIGS. 3 and 4 show the monitoring device 100 in a particular embodiment of the invention. This monitoring device 100 is positioned in a device 200 for guidance of a first threaded tube, for example the female tubular element 16 during its connection by makeup with a second threaded tube, for example the male tubular element 18.

Such a guidance device 200 is more usually known as a stabbing guide. This device 200 comprises a gripping head 202 for the first tube. The means for measuring the dimensional characteristic are preferably arranged at least partially in the gripping head 202. Thus, FIG. 4 shows two measuring units 104 comprising ultrasound transducers 104A and 104C, which are positioned in the gripping head 202 so as to be in contact with or close to the female tubular element. Preferably, the measuring means 102 are housed in the gripping head 202, as illustrated in FIG. 3. In the example illustrated, a cavity 204 is provided inside the gripping head in order to house the transducer 104A. Further, a support 206 is, for example, fixed to the gripping head to allow the transducer 104C to be held in position. As an example, the support comprises a system of the type comprising a flange and spring.

As is conventional, the device 200 also comprises a clamping collar 208 that can surround the gripping head 202.

The principal steps of a monitoring method in accordance with the invention will now be described with reference to FIGS. 1 to 7 described above.

Initially, and in general in order to form the connection illustrated in FIG. 1, the first male tube T1 is pre-assembled on the coupling 12. This step may, for example, be carried out initially in the production shop. The assembly comprising the coupling 12 and the first male tube T1 then forms a first, production shop pre-assembled threaded connection 14 which is then transported, for example to an oil platform (not shown).

The first connection 14 is then, for example, positioned vertically over the oil platform. In the example described, this first connection 14 is held in the vertical position by means of a guidance device 200 or stabbing guide, this device holding it by means of its gripping head 202 via the coupling 12. Thus, in the example illustrated, the coupling 12 has a free female end 16 for connection with one of the male ends 18 of the second male tube T2.

The guidance device 200 in this particular embodiment comprises a housing for the means 102 for measuring the dimensional characteristics of the threaded element during makeup. However, in a variation, the measuring means 102 may be disposed in any other manner that allows the monitoring method to be carried out.

Preferably, the gripping head 202 comprises an internal cylindrical surface 203 which can surround the first element 16 as it is being connected to the second element 18. Preferably, the housing forms a hole 204 in the gripping head 202 opening onto the internal cylindrical surface 203. Hence, when the measuring means 102 are inserted inside the hole, they are in direct contact with the first tubular element so that the measurements can be carried out. Clearly, the position of the hole forming the housing will be carefully selected so as to allow the measurement, for example, to be carried out.

Thus, during insertion of the assembly 10 comprising the coupling connection 12 and the first tube T1, the ultrasound transducers 104 are positioned relative to the coupling connection 12 such that they are capable of measuring the first to third dimensional characteristics.

The order of the monitoring steps is detailed below. During makeup, the means 102 measure the variation with time of a dimensional characteristic of the female element 16 in a pre-defined direction, this element 16 having been disposed inside the guidance device 200.

In this example, the variation of three dimensional characteristics of the female element is measured:
the first characteristic corresponds to the thickness of the female element 16 in a direction radial to the sealing surface;
the second characteristic corresponds to the thickness of the female element 16 in a direction radial to the abutment surface;
the third characteristic corresponds to the length of the female threaded element 16 in an axial direction in its upper radial portion, i.e. above the abutment surfaces.

During a subsequent step, the means 106 analyse the representative curves of these variations with time. Thus, the variation with time of these three dimensional characteristics is respectively shown by the curves in FIGS. 5 to 7. This analysis may, of course, also be carried out directly by a platform operative.

Next, the means 106 identify at least one zone in the profile of the variation of the dimensional characteristic where the slope changes and establish a correspondence between that zone and a makeup state of the threaded connection. This step may be carried out by the analysis means, but also by a platform operative.

Preferably, in order to set up this correspondence, the analysis means 106 compare a model of the profile of the variation made using a mathematical method, for example the finite element method. Next, the analysis means 106 compare the measured profile of the variation with the model profile in order to identify the characteristic zones of the measured profile of the variation.

Preferably and in this example, the unit comprises means for managing the stopping of the makeup of the connection as a function of the result of the variational analysis of the dimensional characteristic. As an example, the means directly manage one working tong. As soon as a pre-defined makeup step has been detected, makeup is halted.

Clearly, other embodiments may be envisaged without departing from the scope of the invention. Thus, a variety of modifications may be made by the skilled person to the invention which has just been described by way of example.

The invention claimed is:

1. A method for monitoring a makeup state of a threaded tubular connection, the threaded connection including a male threaded tubular element and a female threaded tubular element configured to contact along an abutment surface, the method comprising:
during makeup of the male threaded element into the female threaded element, measuring a variation over time of at least one dimensional characteristic of at least one of the elements in a pre-defined direction, the measuring comprising:
measuring a length of the female threaded element in an axial direction in a portion between the abutment surface and an end of the female threaded element near the abutment surface; and
measuring a thickness of the female threaded element in a direction radial to the abutment surface, and
analyzing the variation with time of the characteristic to determine a makeup state for the threaded connection,
wherein the dimensional characteristic is deformation of at least one of the elements and is measured by a propagation time of an ultrasound signal.

2. The method as claimed in claim 1, wherein to measure the dimensional characteristic, the ultrasound signal is emitted into a body of the element and a round trip propagation time of the emitted ultrasound signal is analyzed in the pre-defined direction.

3. The method as claimed in claim 1, wherein the dimensional characteristic represents a thickness in a substantially radial pre-defined direction or a length in a substantially axial pre-defined direction of the threaded element.

4. The method as claimed in claim 1, wherein the dimensional characteristic is measured in a portion of the threaded element including a sealing surface.

5. The method as claimed in claim 1, wherein the variation in the dimensional characteristic corresponds to elongations and/or contractions of the element in the pre-defined direction.

6. The method as claimed in claim 1, further comprising managing stopping of makeup of the connection as a function of the measurement of the dimensional characteristic.

7. A method for connecting a connection, in which a female element and a male element are connected by makeup, employing the monitoring method as claimed in claim 1.

8. The method as claimed in claim 1, a male threaded tubular element and a female threaded tubular element are configured to contact along a sealing surface, the measuring further comprising measuring a thickness of the female threaded element in a direction radial to the sealing surface.

9. The method as claimed in claim 1, wherein at least one zone with a change of slope is identified in a profile of the variation in the dimensional characteristic and a correspondence is established between the zone and a makeup state of the threaded connection.

10. The method as claimed in claim 9, wherein, to establish the correspondence, the profile of the variation is modelled using a mathematical method or a finite element method, and a measured profile of the variation is compared with the model profile.

11. A device for monitoring a makeup state of a threaded tubular connection, the threaded connection including a male threaded tubular element and a female threaded tubular element configured to contact at an abutment surface, the device comprising:
- circuitry configured to measure a variation over time of at least one dimensional characteristic of at least one of the elements in a pre-defined direction, the dimensional characteristic being deformation of at least one of the elements and analyze the variation over time of the characteristic to determine a makeup state of the threaded connection;
- a gripping head configured to grip the male threaded element and the female threaded element;
- a first ultrasonic transducer arranged in the gripping head to measure a length of the female threaded element in an axial direction in a portion between the abutment surface and an end of the female threaded element near the abutment surface; and
- a second ultrasonic transducer arranged in the gripping head to measure a thickness of the female threaded element in a direction radial to the abutment surface.

12. The device as claimed in claim 11, wherein the circuitry is further configured to manage stopping of the makeup of the connection as a function of the measurement of the dimensional characteristic.

13. The device as claimed in claim 11, wherein a male threaded tubular element and a female threaded tubular element are configured to contact along a sealing surface, the device further comprising a third ultrasonic transducer arranged in the gripping head to measure a thickness of the female threaded element in a direction radial to the sealing surface.

* * * * *